(12) United States Patent
Fanget et al.

(10) Patent No.: US 6,231,860 B1
(45) Date of Patent: May 15, 2001

(54) STABILIZERS FOR LIVE VACCINES

(75) Inventors: Bernard Fanget, Saint-Germain-sur-l'Arbresle; Alain Francon, Bessenay, both of (FR)

(73) Assignee: Pasteur Merieux Serums & Vaccins, Lyons (FR)

( * ) Notice: Subject to any disclaimer, the term of this patent is extended or adjusted under 35 U.S.C. 154(b) by 0 days.

(21) Appl. No.: 09/091,542

(22) PCT Filed: Dec. 20, 1996

(86) PCT No.: PCT/FR96/02054

§ 371 Date: Jun. 22, 1998

§ 102(e) Date: Jun. 22, 1998

(87) PCT Pub. No.: WO97/23238

PCT Pub. Date: Jul. 3, 1997

(30) Foreign Application Priority Data

Dec. 22, 1995 (FR) .................................................. 95 15778

(51) Int. Cl.[7] .................................................. A61K 39/00
(52) U.S. Cl. ...................... 424/184.1; 424/204.1; 424/206.1; 424/208.1; 424/209.1; 424/211.1; 424/212.1; 514/53; 514/59; 514/588
(58) Field of Search .............................. 424/184.1, 186.1, 424/204.1, 206.1, 209.1, 211.1, 212.1, 215.1, 229.1, 230.1, 231.1, 278.1, 93.6, 208.1; 514/888, 53, 59, 588

(56) References Cited

U.S. PATENT DOCUMENTS 4,710,378 * 12/1987 Ohtomo .
5,075,110 * 12/1991 Francon et al. .

FOREIGN PATENT DOCUMENTS 299 213   10/1983   (DD) .
0 065 905 12/1982   (EP) .
0 252 059 1/1988    (EP) .
0 353 108 1/1990    (EP) .

OTHER PUBLICATIONS

Database WPI, Week 8208, Derwent Publications Ltd., London, GB; AN 82–14620E, XP002012971 & JP 57 007 423 A (Takeda Chemical Ind KK), Jan. 14, 1982 abstract only.

* cited by examiner

*Primary Examiner*—Jeffrey Stucker
(74) *Attorney, Agent, or Firm*—Burns, Doane, Swecker & Mathis, L.L.P.

(57) ABSTRACT

Stabilizers for live vaccines and attenuated mono- or multivalent live vaccines, stabilized vaccines containig such stabilizers, and methods for preparing such vaccines, are disclosed. Said stabilizers for vaccines containing one or more attenuated live viruses include one or more components selected from each of the following groups: amino acids, disaccharides, polyalcohols and buffer solutions, with the proviso that one component selected from the disaccharide group is saccharose.

37 Claims, No Drawings

STABILIZERS FOR LIVE VACCINES

The present invention relates to stabilizing agents for monovalent or multivalent live vaccines, to the stabilized vaccines containing these agents, and to the processes for preparing such vaccines.

Vaccines which comprise live viruses and, more especially, attenuated live viruses are markedly sensitive to the conditions under which they are prepared and stored. Substantial losses of viral titre are observed during the lyophilization stages, during storage and also during the stages of harvesting the virus following culture. Given the importance of viral titre for immunization efficiency, it is found to be essential to use stabilizing agents in order to safeguard the viral titre to the greatest possible extent. Stabilizing agents are chemical and/or biological compounds which can be added to vaccines at different stages in their preparation with a view to ensuring that the efficiency of the vaccine is at a maximum when it is used, which can sometimes be several years after it was initially stored.

A large number of compounds have been tested for their ability to stabilize different vaccines containing attenuated live viruses. The compounds which have been tested in the prior art (cf., for example, U.S. Pat. No. 3,783,098, U.S. Pat. No. 3,915,794 and EP 028,563), one of the first of which was SPGA, mainly contain bovine or human serum albumin, casein which is hydrolysed to a greater or lesser extent, or gelatin, where appropriate an alkali metal salt of glutamic acid, a sugar (glucose, sucrose or dextran), and a monometallic or dimetallic alkali metal phosphate, or one of their mixtures. EP 065,905 describes a stabilizing compound for the vaccine against yellow fever which is composed of one or more amino acids selected from a group of eleven amino acids, lactose, sorbitol and a phosphate buffer solution (PBS).

However, all these compositions suffer from major drawbacks. In the first place, they contain proteins or protein hydrolysates of animal or human origin (albumins, etc.) which represent a potential biological risk and do not constitute chemically defined components. Furthermore, the compositions of the state of the art do not confer adequate stability on attenuated live vaccines, thereby limiting the possibilities of storing such vaccines and rendering hazardous any possible exposure of the vaccines to elevated temperatures while they are being stored or shipped. Thus, the loss in the activity of these vaccines results in inefficient vaccination and therefore in a vaccination which does not protect in the case of an actual infection. In addition, the efficiency of the known compositions is still more limited when it is a matter of stabilizing the different valencies of a multivalent vaccine containing different viruses. Thus, the tetravalent vaccine MMRV (measles/mumps/rubella/varicella) represents an example of a multivalent vaccine for which is there currently no stabilizer which is adequate for the four valencies.

The stabilizing agents of the invention do not suffer from the abovementioned drawbacks. These stabilizing agents for compositions, in particular vaccines, containing one or more attenuated live viruses, comprise one or more components selected from each of the groups consisting of amino acids, disaccharides, polyalcohols and buffer solutions, with the proviso that one component selected from the disaccharide group is sucrose. In the stabilizing agent of the invention, the component(s) selected from the disaccharide group can be present in a proportion of from 2 to 6%. Advantageously, the component(s) selected from the disaccharide group can be present in a proportion of 2.5%.

The polyalcohol group, which is a component of the stabilizing agent of the invention, can, in particular, include sorbitol and mannitol. The stabilizing agent of the invention can comprise sorbitol and mannitol. When the stabilizing agent of the invention comprises sorbitol, the latter is preferably present in a proportion of from 2 to 6%. When the stabilizing agent of the invention comprises sorbitol, the latter is advantageously present in a proportion of from 3 to 5%. Particularly advantageously, the sorbitol can be present in a proportion of 5%. When the stabilizing agent of the invention comprises mannitol, the latter is preferably present in a proportion of from 1 to 2.5%. When the stabilizing agent of the invention comprises mannitol, the latter is advantageously present in a proportion of 1.5%.

The buffer solution group, which is a component of the stabilizing agent of the invention, can, in particular, include phosphate buffers and ethylenediaminetetraacetic acid (EDTA). Advantageously, the stabilizing agent of the invention comprises a phosphate buffer. The stabilizing agent of the invention can additionally comprise dextran. When the stabilizing agent of the invention comprises dextran, the latter is preferably present in a proportion of from 1 to 4%. When the stabilizing agent of the invention comprises dextran, the latter is advantageously present in a proportion of 3%.

The stabilizing agent of the invention can additionally comprise urea, a urea derivative, or a mixture thereof. Examples of urea derivatives which can be employed are allylurea, acetamide, methyl carbamate or butyl carbamate. When the stabilizing agent of the invention comprises urea, a urea derivative or a mixture thereof, the latter is/are preferably present in a proportion of from 0.125 to 2%. When the stabilizing agent of the invention comprises urea, a urea derivative or a mixture thereof, the latter is/are advantageously present in a proportion of 0.5%.

The pH of the compositions of the invention is preferably adjusted in dependence on the virions to be stabilized. It is particularly advantageous to adjust the pH to 7.

The stabilizing agents of the invention can be used to stabilize a large number of compositions, in particular monovalent vaccines which basically contain one viral strain or species, or multivalent vaccines which contain several viral strains or species. The invention also relates to the compositions, in particular the vaccines, which are stabilized using the abovementioned stabilizing agents.

Such vaccines which have been stabilized in accordance with the invention can, for example, comprise at least one virus of the Herpesviridae family. The Herpesviridae family comprises, in particular, varicella virus, cytomegalovirus and herpes simplex virus. Varicella virus is particularly delicate and thermolabile as compared with other viruses. The stabilizing agents of the invention are therefore of particular relevance when it is a matter of stabilizing a virus which is as unstable as varicella virus.

The stabilizing agents of the invention can be applied to other viruses, which viruses can be selected, in particular, from the Paramyxoviridae (*morbillivirus,* including measles, the mumps virus, *parainfluenza* viruses of types 1, 2, 3 and 4, and *pneumoviruses*), Togaviridae (rubella) and the *influenza* (A, B and C) viruses.

The mixtures which are obtained from the abovementioned viruses or from other viruses and which constitute multivalent vaccines can advantageously be stabilized using the stabilizing agents of the invention. A conceivable multivalent vaccine which may be mentioned is the measles/mumps/rubella vaccine. Within the context of valency combinations, the stabilizing agents of the invention exhibit favourable properties, in addition to the abovementioned advantages, in that their ability to stabilize each of the valencies enables these valencies to be combined. Thus, combining infectious agents for different diseases represents an economic and practical advance to the extent that one prophylactic treatment protects against several diseases, contrary to the situation with monovalent vaccines. However, the coexistence of different infectious agents poses substantial problems of compatibility between these agents, which problems make it difficult to carry out an effective simultaneous polyvaccination. The stabilizing agents of the invention provide a solution to these problems. The preparation of a tetravalent measles/mumps/rubella/varicella vaccine illustrates these problems of vaccine combination since three of the valencies of the combination exhibit thermoinstability. When a stabilizing agent of the invention is used, adequate infective potency is stabilized and preserved in the case of each of the four valencies.

The vaccines are preferably lyophilized, when possible, with a view to improving the stability of the final vaccine still further. When lyophilized live vaccines are being prepared, the said vaccines are preferably brought into contact with an appropriate quantity of stabilizing agent of the invention. The viruses can be brought into contact with the stabilizing agent of the invention before, during or after the harvesting of the said viruses. The viruses are advantageously brought into contact with the stabilizing agent of the invention before the said viruses are harvested.

The invention will be described in more detail in the remainder of the description. By way of illustration, we have chosen to explain, as examples of implementing the invention, the preparation of a stabilized monovalent varicella vaccine and the preparation of a stabilized multivalent measles/mumps/rubella/varicella vaccine, since the problems of stability and combination are particularly pronounced in these cases.

EXAMPLES

Example 1

Preparation of a Varicella Vaccine Which is Stabilized in Accordance with the Invention The attenuated varicella strain which is used for preparing a vaccine which is stabilized in accordance with the invention is the strain OKA.

A stabilizer is prepared using the following components, which are mixed in p.f.i (preparation for injection) water in the following proportions:

sorbitol, 5%, mannitol, 2.5%, sucrose, 5%, dextran, 3%, amino acid mixture, urea, 0.5%,

EDTA, 0.05%, sodium glutamate, 0.05%.

The viruses are harvested or released from the infected cells either by cell disintegration (sonication, shearing, high pressure, etc.) in the stabilizer, or spontaneously in the stabilizer. In this way, a stabilized viral suspension is obtained following clarification.

The test samples are aliquoted into small bottles, after having adjusted the titre by dilution, and then lyophilized using a suitable cycle.

Tests on the Stability of the Resulting Vaccine

The lyophilized preparations to be tested are rehydrated and titred. Activity is determined by the number of plaque-forming units (pfu) by means of counting the cytopathic effects obtained in 25 cm$^2$ dishes at different dilutions of the samples.

The control stabilizer which is used is a traditional stabilizer of known type and corresponds, for example, to that described in U.S. Pat. No. 4,147,772.

Comparative Stability at Different Stages in the Preparation of the Vaccine

|  | Titre (pfu/ml) | |
| --- | --- | --- |
| Test conditions and stages | Control (ex.: SPGA) | Stabilizer of the invention |
| During harvesting | X | x + 1 log |
| Following lyophilization | X | x + 0.2 log |
| Storage at 37° C. for 7 days | X | x + 1.1 log |

In the above table, x is the standard titre.

Stability Obtained Using the Stabilizer of the Invention Under Different Storage Conditions

| Period of storage | Loss of titre at 22.5° (Δpfu/dose) | Period of storage | Loss of titre at 5° (Δpfu/dose) | Period of storage | Loss of titre at −70° (Δpfu/dose) |
| --- | --- | --- | --- | --- | --- |
| 1 month | 0.3 | 6 months | 0 | 9 months | 0.1 |
| 1.5 months | 0.3 | 12 months | 0.1 | 18 months | 0.3 |
| 2 months | 0.46 | 18 months | 0.15 | 30 months | 0.1 |
| 3 months | 0.54 | 24 months | 0.28 | 36 months | 0.06 |
|  |  | 30 months | 0.35 |  |  |
|  |  | 36 months | 0.4 |  |  |

The values shown in the above table were obtained by averaging three samples. The stabilizer of the invention maintains viral titre during the different stages of preparing the vaccine as well as during its storage, which in this case is tested at four different temperatures.

Example 2

Preparation of a Multivalent Measles/Mumps/Rubella/Varicella Vaccine Which is Stabilized in Accordance with the Invention The concentrated measles, mumps, rubella and varicella viral products, which have been stored frozen at low temperature, are thawed and then immediately mixed. This mixture is then aliquoted between the different test samples supplemented with a stabilizing product of the invention, as exemplified in Example 1 above. In this way, the following final solution proportions are obtained: measles: 1.5 volumes; mumps: 0.11 volume; rubella: 1.0 volume and varicella: 2.5 volumes. These different proportions, shown by way of example, can vary depending on the titre of the concentrated viral products and are not limiting.

The test samples are aliquoted into small bottles and then lyophilized in accordance with a standard cycle. The stability tests are carried out by placing the bottles at 37° C. for 7 days or at 22° C. for 21 days or at +4° C. for 30 months.

Stability Obtained with the Stabilizer of the Invention Under Different Storage Conditions

| TEST SAMPLES | Loss of titre (log) | | |
|---|---|---|---|
| | 37° C. for 7 days | 22° C. for 14 days | 22° C. for 21 days |
| Measles | 0.5 | #0 | #0 |
| Muinps | 1 | 0.3 | 0.4 |
| Rubella | 0.09 | #0 | #0 |
| varicella | 1 | 0.15 | 0.16 |

| Test samples at +4° C. | Loss (log) | | | |
|---|---|---|---|---|
| | Measles | Mumps | Rubella | Varicella |
| 3 months | 0.37 | 0.33 | 0.23 | 0.03 |
| 6 months | #0 | 0.03 | 0.16 | 0.06 |
| 9 months | 0.3 | 0.27 | 0.2 | 0.1 |
| 12 months | 0.1 | 0.36 | #0 | #0 |
| 18 months | 0.23 | 0.6 | 0.07 | 0.1 |
| 24 months | 0.33 | 0.34 | 0.07 | 0.3 |
| 30 months | 0.63 | 0.43 | 0.4 | 0.25 |

No loss is observed which is significantly different from that obtained in the case of the corresponding monovalent vaccines.

What is claimed is:

1. A stabilizing agent for live attenuated viral vaccines which is free of protein of animal origin comprising: dextran, one or more components selected from the group consisting of urea and urea derivatives, and one or more components selected from each of the following groups: amino acids, disaccharides, polyalcohols, and buffer solutions with the proviso that one component selected from the disaccharide group is sucrose.

2. The stabilizing agent of claim 1, wherein the component(s) selected from the disaccharide group is or are present in a proportion of from 2 to 6%.

3. The stabilizing agent of claim 2, wherein the component(s) selected from the disaccharide group is or are present in a proportion of 2.5%.

4. The stabilizing agent of claim 1, wherein the polyalcohol group is sorbitol and/or mannitol.

5. The stabilizing agent of claim 4, comprising sorbitol and mannitol.

6. The stabilizing agent of claim 4, wherein sorbitol is present in a proportion of from 2 to 6%.

7. The stabilizing agent of claim 6, wherein sorbitol is present in a proportion of 5%.

8. The stabilizing agent of claim 4, wherein mannitol is present in a proportion of from 1 to 2.5%.

9. The stabilizing agent of claim 8, wherein mannitol is present in a proportion of 2.5%.

10. The stabilizing agent of claim 1, wherein the buffer solution group is a phosphate buffer and/or ethylenediaminetetraacetic acid.

11. The stabilizing agent of claim 10, comprising a phosphate buffer.

12. The stabilizing agent of one of claims 1 to 11, wherein dextran is present in a proportion of from 1 to 4%.

13. The stabilizing agent of claim 12, wherein dextran is present in a proportion of 3%.

14. The stabilizing agent of claim 1, wherein the component(s) selected from the group consisting of urea and urea derivatives is or are present in a proportion of from 0.125 to 2%.

15. The stabilizing agent of claim 14, wherein the component(s) is or are present in a proportion of 0.5%.

16. The stabilizing agent of claim 1, wherein the pH is adjusted to 7.

17. A stabilized, attenuated live virus vaccine which comprises a stabilizing agent according to claim 1.

18. The vaccine of claim 17 which comprises at least one virus of the herpes family.

19. The vaccine of claim 18, wherein the herpes family comprises varicella virus, cytomegalo-virus and herpes simplex virus.

20. The vaccine of claim 19 which comprises varicella virus.

21. The vaccine of claim 17 which comprises at least one virus selected from the group consisting of measles, mumps, parainfluenza types 1, 2, 3 and 4 viruses, pneumoviruses, rubella, influenza A, influenza B and influenza C viruses.

22. The vaccine of claim 21 which comprises the measles, rubella and mumps viruses.

23. The vaccine of claim 22 which further comprises varicella virus.

24. A stabilized composition which comprises the stabilizing agent of claim 1.

25. A process for preparing stabilized vaccines containing attenuated live viruses, said process comprising contacting attenuated live viruses with an effective amount of the stabilizing agent of claim 1.

26. The process of claim 25, wherein said contacting is conducted prior to a lyophilization step.

27. The process of claim 25, wherein said viruses are brought into contact with the stabilizing agent before the viruses are harvested.

28. A stabilizing agent for live attenuated viral vaccines which is free of protein of animal origin comprising dextran, and at least one component from each of the following groups:

(a) urea and urea derivatives, (b) amino acids, (c) disaccharides and (d) polyalcohols, wherein the components are in a buffer solution with the proviso that one component selected from the disaccharide group is sucrose.

29. The stabilizing agent of claim 28, wherein the component(s) selected from the disaccharide group is or are present in a proportion of from 2 to 6%.

30. The stabilizing agent of claim 28, wherein the polyalchohol group is sorbitol and/or mannitol.

31. The stabilizing agent of claim 28, wherein the buffer solution is a phosphate buffer.

32. The stabilizing agent of claim 31 wherein the buffer solution further comprises ethylenediaminetetraacetic acid.

33. The stabilizing agent of claim 28, wherein dextran is present in a proportion of from 1 to 4%.

34. The stabilizing agent of claim 28, wherein the pH is adjusted to 7.

35. A stabilized, attenuated live virus vaccine which comprises a stabilizing agent according to claim 28.

36. A stabilized composition which comprises the stabilizing agent of claim 28.

37. A process for preparing stabilized vaccines containing attenuated live viruses, said process comprising contacting attenuated live viruses with an effective amount of the stabilizing agent of claim 28.

* * * * *